(12) United States Patent
Ernst et al.

(10) Patent No.: US 7,045,641 B2
(45) Date of Patent: May 16, 2006

(54) PROCESS FOR PREPARING POLYENEDIALDEHYDE MONOACETALS

(75) Inventors: Hansgeorg Ernst, Speyer (DE); Klaus Henrich, Hassloch (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 721 days.

(21) Appl. No.: 10/336,827

(22) Filed: Jan. 6, 2003

(65) Prior Publication Data

US 2003/0158427 A1    Aug. 21, 2003

(30) Foreign Application Priority Data

Jan. 4, 2002    (DE) ................ 102 00 130

(51) Int. Cl.
  *C07D 317/26*    (2006.01)
  *C07D 319/06*    (2006.01)
  *C07C 45/48*    (2006.01)

(52) U.S. Cl. ............. 549/375; 549/453; 568/460

(58) Field of Classification Search ........... 549/375, 549/453; 568/460
  See application file for complete search history.

(56) References Cited

U.S. PATENT DOCUMENTS 4,268,444 A    5/1981   Jaedicke .............. 260/340
  2002/0128519 A1   9/2002   Ernest et al. ............. 568/460

OTHER PUBLICATIONS

Hagen et al. "Synthesis of Donor-Acceptor Substituted Polyenes" Synthetic Metals vol. 41-43 (1991) pp. 1557-1561.
Chopra et al. "Synthesis of the Enolic β-Diketone Carotenoids, Mytiloxanthin and Trikentriofhodin" J.C.S. Chem. Comm. (1977) pp. 467-468.
Chopra et al. "Carotenoids and Related Compounds. Part 41 Structure of Mytiloxanthin and Synthesis of a cis Isomer" J. Chem. Soc. Perkin. Trans. (1988) pge 1383-1388.
Hansgeorg Ernst "Recent advances in industrial carotenoid synthesis" Pure Appl. Chem. vol. 74, No. 11, (2002) pp. 2149-2162.

*Primary Examiner*—Taofiq Solola
(74) *Attorney, Agent, or Firm*—Keil & Weinkauf

(57) ABSTRACT

A process for preparing compounds of the formula I

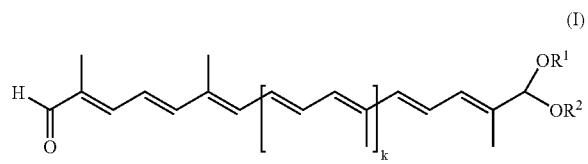

is described and entails converting a compound of the formula II

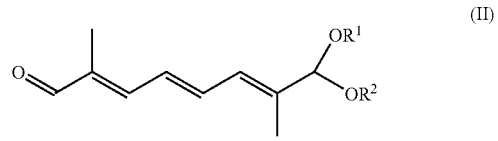

by Wittig or Wittig-Horner reaction into a compound of the formula IV,

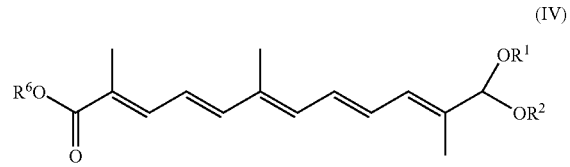

where appropriate converting the compound of the formula IV by hydrolysis of the acetal function and Wittig or Wittig-Horner reaction into a compound of the formula VI

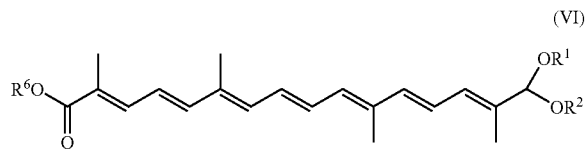

and converting the compound of the formula IV or VI in two stages into the compound of the formula I. The radicals $R^1$, $R^2$ and $R^6$ and k have the meaning indicated in the description. Novel intermediates are also described.

10 Claims, No Drawings

PROCESS FOR PREPARING POLYENEDIALDEHYDE MONOACETALS

FIELD OF INVENTION

The present invention relates to a process for preparing $C_{15}$ or $C_{20}$ polyenedialdehyde monoacetals.

Such polyene building blocks protected at one end are of great interest for the selective synthesis of various $C_{40}$ carotenoids with an asymmetric structure through successive reaction of the $C_{15}$ dialdehyde building block with appropriately functionalized $C_{15}$ or $C_{10}$ building blocks or of the $C_{20}$ dialdehyde building block with appropriately functionalized different $C_{10}$ building blocks. The $C_{40}$ carotenoids with an asymmetric structure include, for example, capsanthin and cryptocapsin, and α-carotene or β-cryptoxanthin.

BACKGROUND OF THE INVENTION

DE-A 2851051 describes the preparation of 11-(5,5-dimethyl-1,3-dioxan-2-yl)-2,4,6,8,10-dodecapentaenal by Wittig or Wittig-Horner olefination with 2,6-dimethylocta-2,4,6-triene-1,8-dial with a suitable $C_5$ building block under specific reaction conditions. The disadvantage of this process is, however, that the asymmetric $C_{10}$ dialdehyde employed is not a synthon which is customary on the industrial scale.

Synth. Met. 42, 1557 (1991) describes the preparation of crocetindial mononeopentyl glycol acetal by partial hydrolysis of crocetindial bisneopentyl glycol acetal. The monoacetal is purified by chromatography. The selectivity of a partial acetal cleavage is normally inadequate, which makes the process described appear undesirable for an industrial process.

J. Chem. Soc., Chem. Commun. 1977, 467 and J. Chem. Soc. Perkin Trans 1 (1988) 1383 describes the preparation of methyl 11-(1,3-dioxolan-2-yl)-2,6-dimethyl-2,4,6,8,10-dodecapentaenoate by acetalization of the aldehyde with ethylene glycol.

BRIEF SUMMARY OF THE INVENTION

It is an object of the present invention to provide a process which can be implemented on the industrial scale and is flexible in relation to the protective group for preparing $C_{15}$ and $C_{20}$ dialdehyde monoacetals.

We have found that this object is achieved by a process for preparing compounds of the formula I

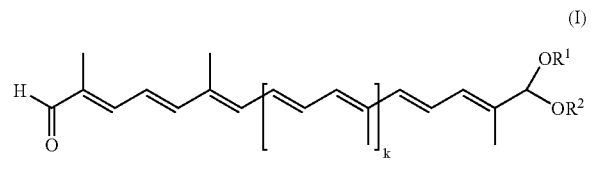

in which a) a compound of the formula II

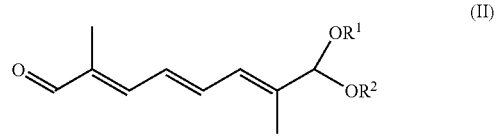

is converted by reaction with a reagent of the formula III

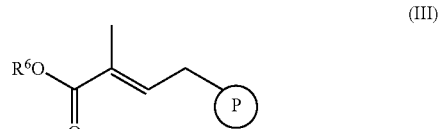

into a compound of the formula IV,

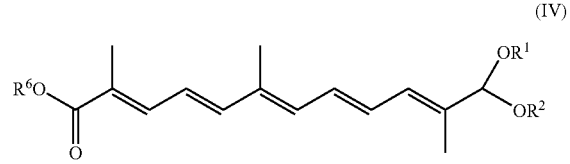

b) where appropriate the compound of the formula IV is converted by hydrolysis of the acetal function and reaction with a reagent of the formula V

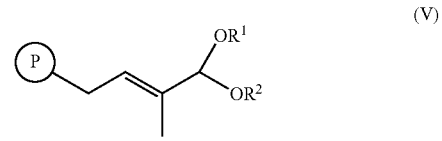

into a compound of the formula VI

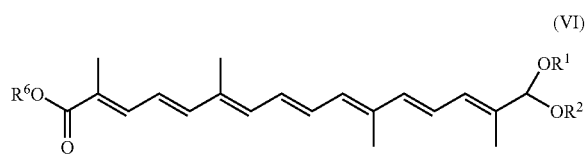

c) the compound of the formula IV or VI is reduced to a compound of the formula VII

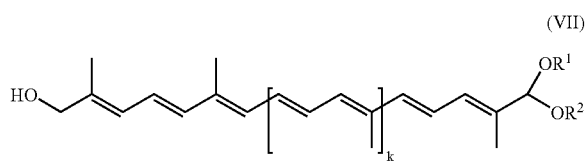

d) the compound of the formula VII is oxidized to the compound of the formula I, in which $R^1$ and $R^2$ are, independently of one another, $C_1$–$C_8$-alkyl or, together with the oxygen atoms to which they are bonded, and with the carbon atom located between them, are

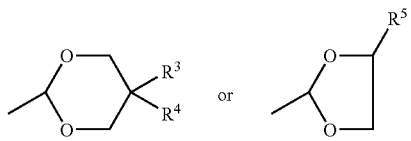

in which $R^3$, $R^4$ and $R^5$ are, independently of one another, hydrogen or $C_1$–$C_4$-alkyl, $R^6$ is $C_1$–$C_8$-alkyl, (P)

is a triarylphosphonium or phosphonic acid dialkyl ester radical, and k is 0 or 1.

In the case of open-chain acetals, alkyl radicals which may be mentioned for $R^1$ and $R^2$ are linear or branched $C_1$–$C_8$-alkyl chains, e.g. methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl and n-octyl. Preferred alkyl radicals for $R^1$ and $R^2$ are methyl, ethyl, n-propyl and 1-methylethyl, particularly preferably methyl and ethyl.

Alkyl radicals which may be mentioned for $R^3$ to $R^5$ are linear or branched $C_1$–$C_4$-alkyl chains, e.g. methyl, ethyl, n-propyl, 1-methylethyl, n-butyl, 1-methylpropyl, 2-methylpropyl and 1,1-dimethylethyl. Preferred radicals for $R^3$ to $R^5$ are hydrogen and methyl.

DETAILED DESCRIPTION THE INVENTION

Compounds of the formula II are known and can be obtained, for example, by p-toluenesulfonic acid-catalyzed acetalization of 2,7-dimethylocta-2,4,6-triene-1,8-dial, compare *Helv. Chim. Acta* 1981, 64 (7), 2469. A preferred process for preparing the compounds of the formula II is described in the earlier application DE 101 12 067.2. In this case, a 3-methyl-2-butene-1,4-dial monoacetal is reacted with a reagent of the above formula III, the resulting acetal ester is reduced to the alcohol, and the alcohol is oxidized to a compound of the formula II.

Preference is given to the use of a compound of the formula IIa,

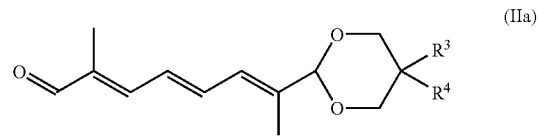

in which $R^3$ and $R^4$ are identical and are hydrogen or methyl.

In step a) of the process of the invention, the compound of the formula II is reacted with a reagent of the formula III in a Wittig or Wittig-Horner reaction.

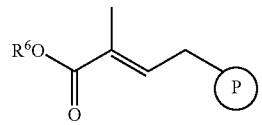

(P) in the formula III can be a triarylphosphonium radical $P(R^8)_3^+$, where $R^8$ is the usual radicals occurring in phosphines and phosphonium salts, such as phenyl, tolyl, naphthyl, each of which may be substituted where appropriate. $R^8$ is preferably phenyl. The positive charge on the triarylphosphonium radical is compensated by an anion equivalent $X^-$ of an inorganic or organic acid, preferably a strong inorganic or organic acid.

The term strong acid encompasses hydrohalic acids, in particular hydrochloric acid and hydrobromic acid, sulfuric acid, phosphoric acid, sulfonic acids and other inorganic or organic acids with a comparable degree of dissociation. Strong organic acids in this context also mean $C_1$–$C_6$-alkanoic acids such as formic acid, acetic acid, propionic acid, butyric acid and caproic acid.

The anions of hydrochloric acid, hydrobromic acid, sulfuric acid, phosphoric acid, formic acid, acetic acid and/or sulfonic acids are particularly preferred. $Cl^-$, $Br^-$ and the anions of alkanesulfonic acids having 1 to 4 carbon atoms, benzenesulfonic acid, p-toluenesulfonic acid or trifluoromethanesulfonic acid are very particularly preferred.

Alternatively, (P) is a phosphonic acid dialkyl ester radical $PO(OR^7)_2$ in which $R^7$ is $C_1$–$C_8$-alkyl. In a preferred embodiment of the process of the invention there is use in step a) of a reagent of the formula IIIa

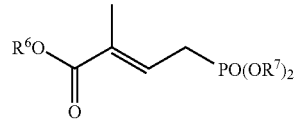

in which $R^6$ has the meaning already indicated, and $R^7$ is $C_1$–$C_3$-alkyl.

The reaction between the compound of the formula II and the reagent of the formula III is carried out under conditions typical of a Wittig or Wittig-Horner reaction, cf., for example, Carotenoids, Vol. 2 "Synthesis", p. 79 et seq.; Birkhäuser Verlag, 1996, and the literature cited therein.

The condensation of II with a compound of the formula III in which (P) is a triarylphosphonium radical can be carried out for example in an inert organic solvent, e.g. in open-chain or cyclic ethers such as diethyl ether, diisopropyl ether, methyl tert-butyl ether, 1,4-dioxane or tetrahydrofuran, in halogenated hydrocarbons such as dichloromethane, chloroform, in aromatic hydrocarbons such as toluene, xylene or benzene or in polar solvents such as dimethylformamide, dimethyl sulfoxide or acetonitrile. Preferred solvents are toluene, tetrahydrofuran and dimethyl sulfoxide or mixtures thereof.

It is possible to use as base all bases customary for Wittig condensations, e.g. alkali metal hydroxides such as sodium hydroxide, potassium hydroxide or lithium hydroxide; alkali metal hydrides such as sodium hydride or potassium hydride; or alkali metal alcoholates such as sodium methoxide or sodium ethoxide. Suitable bases are additionally organolithium compounds such as, for example, n-butyllithium, tert-butyllithium, phenyllithium or alkali metal amides such as lithium, potassium or sodium amide, lithium diisopropylamide, but also alkali metal hexamethyldisilazides.

If $X^-$ is a halide anion, it is also possible advantageously to employ oxiranes as latent bases (see Chem. Ber. 1974, 107, 2050).

The bases preferably used for this Wittig reaction are solutions of alkali metal alcoholates in the corresponding alcohol or oxiranes, especially 1,2-epoxybutane, without additional solvent or mixed with one of the abovementioned solvents or with a lower alkanol.

The amount of base employed is usually in the range from 0.8 to 5 mol, preferably 1 to 3 mol, per mole of the phosphonium salt III employed.

The typical conditions for the Wittig-Horner reaction are likewise used for the reaction of II with a compound of the formula III in which (P) is a phosphonic acid dialkyl ester radical. In this case too, one of the aforementioned inert organic solvents is preferably used, and the base preferably employed is the solution of an alkali metal alcoholate in the corresponding alkanol. However, it is also possible in the case of the Wittig-Horner reaction to use the bases additionally mentioned above for the Wittig reaction with the exception of the oxiranes.

Step b) in the process of the invention is optional. In step b), the $C_{15}$ building block IV is converted into a $C_{20}$ building block of the formula IV which is extended by five carbon atoms. For this purpose, firstly the acetal function in the compound of the formula IV is hydrolyzed to the aldehyde function. Suitable in principle for this are all the conditions known to the skilled worker for preferably acid-catalyzed acetal cleavages, e.g. with dilute mineral acids such as sulfuric acid. It has proved to be particularly suitable to catalyze the hydrolysis of the acetal function with citric acid. Citric acid is expediently employed in an amount of from 5 to 50 mol %, preferably 20 to 30 mol %, based on the compound of the formula IV. The hydrolysis preferably takes place in aqueous media, in particular in a mixture of water with a water-miscible organic solvent such as $C_1$–$C_4$-alkanols, e.g. ethanol, at a temperature which is suitably from 0° C. to the boiling point of the solvent, preferably 25 to 55° C.

The resulting ester aldehyde is then reacted with a reagent of the formula V

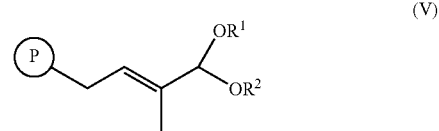

in which $R^1$, $R^2$ and (P) have the meanings already indicated. The reaction takes place under conditions which are typical of a Wittig or Wittig-Horner reaction, concerning which reference is made to the statements above.

Compounds of the formula V are known per se. They can be obtained, for example, from β-formylcrotyl acetate. Their preparation is described, for example in Carotenoids, Vol. 2 "Synthesis", p. 115 et seq., Birkhäuser Verlag, 1996.

A reagent of the formula Va $$X^{\ominus} \; (R^8)_3 \overset{\oplus}{P} \diagup\!\!\!\diagdown \diagup\!\!\!\diagdown \overset{OR^1}{\underset{OR^2}{}}$$

in which $R^1$, $R^2$, $R^8$ and $X^-$ have the meaning already indicated, is preferably employed in step b).

In steps c) and d) of the process of the invention the ester function in the compound of the formula IV or VI is converted into the aldehyde function in two steps.

The two-stage conversion has proved to be more favorable than direct conversion of the ester into the aldehyde. In step c), the ester function is firstly reduced to the alcohol. It is possible in principle to employ for this step all reagents known to the skilled worker for reducing esters to alcohols, preferably hydride reagents, for example alkali metal borohydrides or alkali metal aluminum hydrides.

In a preferred embodiment of the process step c), the ester function is reduced using a sodium aluminum hydride compound, particularly preferably sodium dihydrobis(2-methoxyethoxy)aluminate. The commercially available concentrated toluene solution of sodium dihydrobis(2-methoxyethoxy)aluminate ("Vitride®") is particularly advantageous. This reagent is not pyrophdric, not sensitive to oxygen (GIT Fachz. Lab. 9/96, 914) and, as a liquid, is considerably easier to handle in an industrial process than are solid complex hydrides such as, for example, lithium aluminum hydride.

The reaction is preferably carried out in such a way that the ester of the formula IV or VI is introduced into a solvent which is inert toward hydride reagents, such as aromatic hydrocarbons, for example toluene, open-chain or cyclic ethers, glycol ethers or a mixture of these solvents, and the reducing agent is metered in at a temperature in the range from −20° C. to 30° C., preferably from −10° C. to 10° C., particularly preferably from −5° C. to 0° C.

It is usual to employ at least two equivalents of hydride per equivalent of ester, i.e. at least 0.5 mol of lithium aluminum hydride/mole of ester or 1.0 mol of Vitride/mole of ester. However, in order to achieve complete conversion, it is advantageous to employ a certain excess of reducing agent. This excess is in the range from 10 to 50 mol %, preferably 20 to 30 mol %.

In the preferred embodiment of the process of the invention, the ester of the formula IV or VI is reduced with the toluene solution of Vitride to the alcohol VII. An aqueous work-up results in a virtually quantitative yield of a crude product which can be employed directly, without purification, in the next stage d).

Suitable for oxidizing the compound of the formula VII to the compound of the formula I in step d) of the process of the invention are the oxidation processes known to the skilled worker for converting polyene alcohols into polyene aldehydes, which are described, for example, in DE-A-3705785, DE-A-4440286, DE-A-4440287 and in EP-A-0 718 283. However, catalytic methods will be preferred from the economic, ecological and technical viewpoints of the process. Catalysts which can be employed for this purpose are, inter alia, ruthenium compounds such as tetrapropylammonium perruthenate, tris(triphenylphosphine)ruthenium (II) chloride or 1,5-cyclooctadieneruthenium(II) chloride in amounts of from 2 to 4 mol % in the presence of an at least stoichiometric amount of 4-methylmorpholine N-oxide as co-oxidant (see J. Chem. Soc. Chem, Commun. 1987, 1625).

However, the compound of the formula VII is preferably oxidized with oxygen in the presence of an N-oxyl radical and of a copper(I) compound. The N-oxyl radicals are normally derived from secondary amines in which all the substituents on the carbon atoms α to the nitrogen atom are different from hydrogen. Examples of suitable N-oxyl radicals are 2,2,6,6-tetramethylpiperidin-1-oxyl and 4-hydroxy-2,2,6,6-tetramethylpiperidin-1-oxyl. Copper(I) chloride is preferred as copper(I) compound. The catalytic oxidation of VII to I moreover preferably takes place with a mixture which comprises 2,2,6,6-tetramethylpiperidin-1-oxyl/copper(I) chloride/dimethylformamide/oxygen or with a mixture which comprises 4-hydroxy-2,2,6,6-tetramethylpiperidin-1-oxyl/copper(I) chloride/dimethylformamide/oxygen, in dimethylformamide as solvent. Further details of the oxidation are to be found inter alia in DE-A-3705785 and EP-A-0 718 283.

The invention additionally relates to compounds of the formula

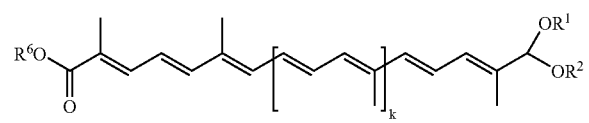

in which $R^1$, $R^2$, $R^6$ and k have the meanings already indicated, and in the case where $R^1$ and $R^2$ together with the oxygen atoms to which they are bonded, and with the carbon atom located between them, are

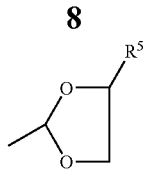

$R^5$ is not hydrogen if k is 0 and $R^6$ is methyl.

Preferred compounds have the formula

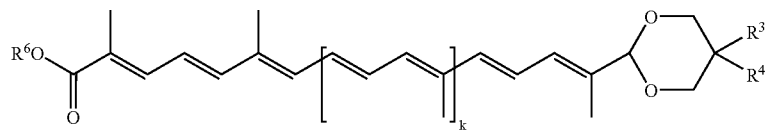

in which $R^6$ is $C_1$–$C_4$-alkyl, and $R^3$ and $R^4$ are identical and are either hydrogen or methyl.

The invention additionally relates to compounds of the formula VII

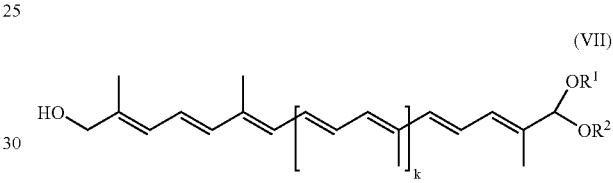

in which $R^1$, $R^2$ and k have the meanings already indicated.

Preferred compounds have the formula

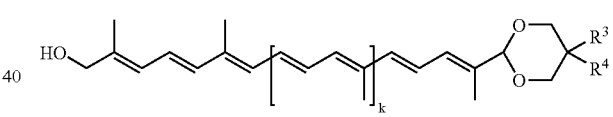

in which $R^3$ and $R^4$ are identical and are hydrogen or methyl.

The invention additionally relates to compounds of the formula I

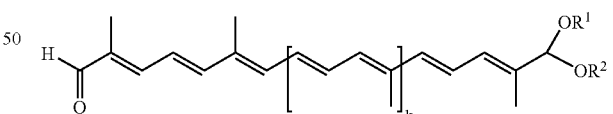

in which $R^1$, $R^2$ and k have the meaning already indicated, and in the case where $R^1$ and $R^2$ together with the oxygen atoms to which they are bonded, and with the carbon atom located between them, are

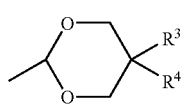

$R^3$ and $R^4$ are not both methyl.

The invention is illustrated in detail by the following examples.

EXAMPLE 1

11-(5,5-Dimethyl-1,3-dioxan-2-yl)-2,6-dimethyl-2,4,6,8,10-dodecap entaenal a) Ethyl 11-(5,5-dimethyl-1,3-dioxan-2-yl)-2,6-dimethyl-2,4,6,8,10-dod ecapentaenoate 62.6 g (0.25 mol) of 2,7-dimethyl-2,4,6-octatriene-1,8-dial mononeopentyl acetal and 79.3 g (0.30 mol) of ethyl 4-(diethylphosphono)-2-methyl-2-butenoate were introduced into 625 ml of dichloromethane. At 0° C., 112.3 g of a 20% strength ethanolic solution of sodium ethoxide (0.33 mol) were run in over the course of 60 minutes. The mixture was stirred at 0° C. for 1 hour and then at room temperature for 24 hours. Thereafter 100 ml of 10% strength aqueous acetic acid and 250 ml of semiconcentrated brine were added to the mixture. The organic phase was separated off, washed once each with 250 ml of semiconcentrated brine and water, dried over sodium sulfate and concentrated in vacuo at 60° C.

Yield: 101.4 g of reddish brown viscous oil.

For characterization, the crude product was dissolved by heating in a mixture of 600 ml of isobutanol and 5 ml of triethylamine. After cooling to 0° C. and stirring at 0° C. for 2 hours, the crystals which had formed were filtered off. The filter cake was washed with cold isobutanol and dried under a stream of nitrogen. Yield of crystals: 51.5 g (57.2% of theory). Melting point 118.5 to 119° C. $E^1_1$ ($CHCl_3$): 2055 (370 nm), 1818 (390 nm).

The filtrate was concentrated in vacuo at 50° C. 52.8 g of reddish brown oil were obtained.

b) 11-(5,5-Dimethyl-1,3-dioxan-2-yl)-2,6-dimethyl-2,4,6,8,10-dod ecapentaenol 27.05 g (75 mmol) of the crystalline product from step a) were dissolved in 300 ml of THF. At 0° C., 23.8 g of a 70% strength toluene solution of sodium dihydrobis(2-methoxyethoxy)aluminate and 300 ml of toluene were run in over the course of one hour. The reaction mixture was diluted at 0° C. with 300 ml of hexane. 300 ml of semiconcentrated brine were run in at 0 to 5° C. The aqueous phase was separated off and extracted twice with 300 ml each time of a toluene/n-hexane mixture (1:1 vol/vol). The combined organic phases were washed once with 300 ml of semiconcentrated brine, dried over sodium sulfate and concentrated in a rotary evaporator. The residue (28.8 g) was purified by flash chromatography on silica gel (eluent: cyclohexane/ethyl acetate 10:1). 14.5 g (61.4% of theory) of the title compound were obtained. For characterization, a sample was crystallized from diisopropyl ether. Yellow crystals with melting point 136 to 137° C. were obtained. $E^1_1$ ($CHCl_3$): 1096 (333 nm), 2668 (350 nm), 2495 (339 nm).

c) 11-(5,5-Dimethyl-1,3-dioxan-2-yl)-2,6-dimethyl-2,4,6,8,10-dod ecapentaenal 3.17 g of the product from step b) were dissolved in 12.5 ml of dimethylformamide. 79.7 mg (0.5 mmol) of 2,2,6,6-tetramethylpiperidin-1-oxyl and 51.03 mg (0.5 mmol) of copper(I) chloride were added. Oxygen was then passed in at 20 to 25° C. for 3 hours. The same amount of both catalysts was again added, and oxygen was passed in at 20 to 25° C. for a further hour. The reaction mixture was mixed with 50 ml each of semiconcentrated brine and ethyl acetate. The aqueous phase was separated off and extracted three times with 50 ml of ethyl acetate each time. The combined organic phases were washed with 50 ml of semiconcentrated brine, dried over sodium sulfate and concentrated in a rotary evaporator. The residue (3.52 g) was purified by flash chromatography on silica gel (eluent: cyclohexane/ethyl acetate 8:1). 2.33 g (73.7% of theory) of the title compound were obtained. For characterization, a sample was recrystallized from diisopropyl ether. Melting point 139.5 to 140° C., $E^1_1$ ($CHCl_3$): 2052 (385 nm), 1969 (401 nm).

EXAMPLE 2

15-(5,5-Dimethyl-1,3-dioxan-2-yl)-2,6,11-trimethyl-2,4,6,8,10,12,14-hexadecaheptaenal (Crocetindial Mononeopentyl Glycol Acetal)

a) Ethyl 11-(5,5-dimethyl-1,3-dioxan-2-yl)-2,6-dimethyl-2,4,6,8,10-dodecapentaenoate The compound was prepared as described in Example 1, step a). The residue on evaporation was used without further purification in the following step b).

b) Ethyl 2,6,11-trimethyl-12-oxo-2,4,6,8,10-dodecapentaenoate 52.8 g of the residue on evaporation from step a) were dissolved in 440 ml of ethanol. A solution of 6.16 g (29.3 mmol) of citric acid monohydrate in 100 ml of water was added, and the mixture was heated at 50° C. for 1 hour. It was then cooled to 0° C. and stirred at 0° C. for 24 hours. The crystals were filtered off with suction, washed twice with 50 ml of an ethanol/water mixture (8:2 vol./vol.) each time and once with 50 ml of hot water and then dried to constant weight in a vacuum oven at 50° C. Yield 10.1 g, melting point 120–121° C.

c) Ethyl 15-(5,5-dimethyl-1,3-dioxan-2-yl)-2,6,11-trimethyl-2,4,6,8,10,12,14-hexadecaheptaenoate 13.7 g (50 mmol) of the product from step b) were dissolved in 125 ml of dichloromethane. 25.7 g (55 mmol) of 3-(5,5-dimethyl-1,3-dioxan-2-yl)but-2-enyltriphenylphosphonium chloride were added. At 0° C., 20.4 g of a 20% strength ethanolic solution of sodium ethoxide (60 mmol) were added over the course of 1 hour. The mixture was stirred at 0° C. for 1 hour and then 50 ml of semiconcentrated brine were added. The organic phase was separated off, washed once with 50 ml of semiconcentrated brine, dried over sodium sulfate and concentrated in a rotary evaporator at 20° C. down to 20 mbar. The residue (38.2 g) was purified by flash chromatography on silica gel (eluent: cyclohexane/methyl t-butyl ether 4:1). 19.9 g (93.4% of theory) of the title compound were obtained. For characterization, the product was dissolved by heating in 100 ml of ethyl acetate. 50 ml of diisopropyl ether were added to the hot solution and, after cooling to 0° C., the mixture was stirred for 1 hour. The crystals which formed were filtered off, washed with cold ethyl acetate/diisopropyl ether mixture (2:1 vol./vol.) and dried in a stream of nitrogen. Yield: 8.9 g of red crystals. Melting point 157.5 to 158° C. $E^1_1$ ($CHCl_3$): 2495 (423 nm), 2243 (448 nm).

d) 15-(5,5-Dimethyl-1,3-dioxan-2-yl)-2,6,11-dimethyl-2,4,6,8,10,12,14-hexadecaheptaenol 42.3 g of the product from step c) were dissolved in 400 ml of tetrahydrofuran. At 0° C., 31.8 g of a 70% strength toluene solution of sodium dihydridobis(2-methoxyethoxy)aluminate and 400 ml of toluene were run in over the course of one hour, and the mixture was stirred at 0° C. for 1 hour. The reaction mixture was then diluted with 400 ml of n-hexane and, over the course of 15 minutes, 400 ml of semiconcentrated brine were run in. The aqueous phase was extracted twice with 400 ml of a 1:1 toluene/hexane mixture (vol./vol.) each time. The combined organic phases were dried over sodium sulfate and concentrated in a rotary evaporator at 50° C. down to 20 mbar. The residue was purified by flash chromatography on silica gel (eluent: cyclohexane/ethyl acetate 10:1). 20.12 g (55.2% of theory) of the title compound were obtained. The product was employed in this form in the following step e). $E^1_1$ (CHCl$_3$) 1579 (383 nm), 2668 (405 nm), 2919 (3430 nm).

e) Crocetindial Mononeopentyl Glycol Acetal 3.09 g of the product from step d) were dissolved in 11 ml of dimethylformamide. 64 mg (0.4 mmol) of 2,2,6,6-tetramethylpiperidin-1-oxyl and 41 mg (0.4 mmol) of copper(I) chloride were added. Oxygen was then passed in at 20 to 25° C. for 3 hours. The same amount of both catalysts was then again added, and oxygen was passed in for a further hour. The mixture was then mixed with 40 ml of semiconcentrated brine and 40 ml of ethyl acetate. The aqueous phase was separated off and extracted with 40 ml of ethyl acetate. The combined organic phases were dried over sodium sulfate and concentrated in a rotary evaporator. The residue was purified by flash chromatography on silica gel (eluent cyclohexane/ethyl acetate 10:1). 1.3 g (43% of theory) of crocetindialdehyde mononeopentyl glycol acetal were obtained. For characterization, a sample was recrystallized from ethyl acetate/diisopropyl ether. Melting point 183.5 to 184° C. $E^1_1$ (CHCl$_3$) 2434 (438 nm).

We claim:

1. A process for preparing compounds of the formula I

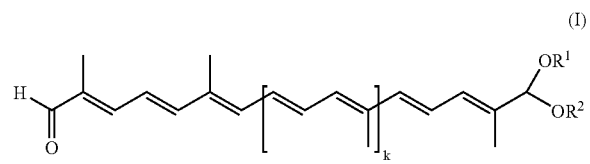

in which a) a compound of the formula II

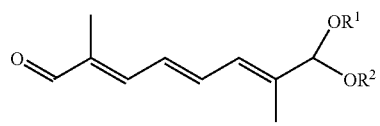

is reacted with a reagent of the formula III

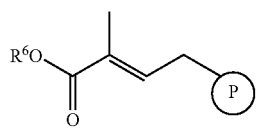

to obtain a compound of the formula IV,

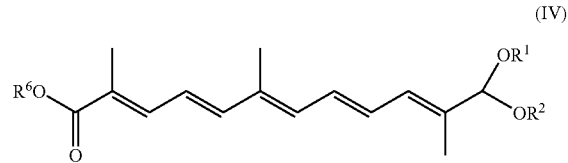

b) optionally, the compound of the formula IV is treated to hydrolyze the acetal function thereof, and reacted with a reagent of the formula V

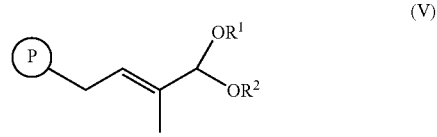

to obtain a compound of the formula VI

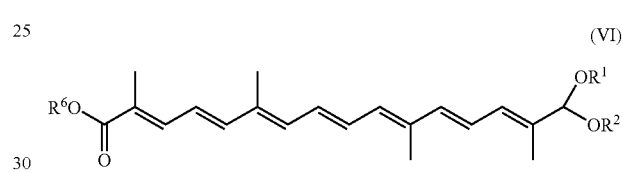

c) the compound of the formula IV or VI is reduced to obtain a compound of the formula VII

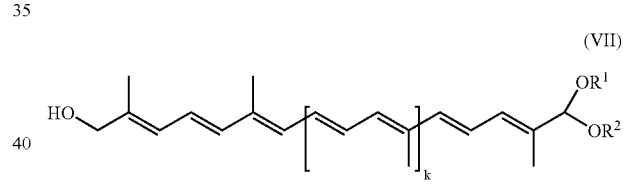

d) the compound of the formula VII is oxidized to obtain the compound of the formula I, in which $R^1$ and $R^2$ are, independently of one another, $C_1$–$C_8$-alkyl or, together with the oxygen atoms to which they are bonded, and with the carbon atom located between them, are

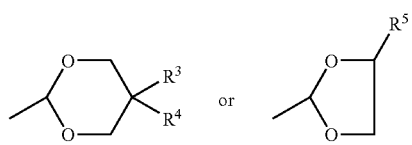

in which $R^3$, $R^4$ and $R^5$ are, independently of one another, hydrogen or $C_1$–$C_4$-alkyl, $R^6$ is $C_1$–$C_8$-alkyl,

Ⓟ is a triarylphosphonium or phosphonic acid dialkyl ester radical, and k is 0 or 1.

2. A process as claimed in claim 1, in which a compound of the formula IIa

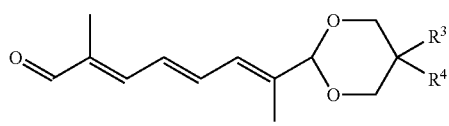
(IIa)

in which $R^3$ and $R^4$ are identical and are hydrogen or methyl, is employed in step a).

3. A process as claimed in claim 1, in which a reagent of the formula IIIa

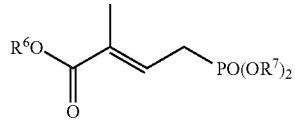
(IIIa)

in which $R^6$ has the meaning indicated in claim 1, and $R^7$ is $C_1$–$C_3$-alkyl, is employed in step a).

4. A process as claimed in claim 1, in which the hydrolysis of the acetal function in step b) is catalyzed with citric acid.

5. A process as claimed in claim 1, in which a reagent of the formula Va

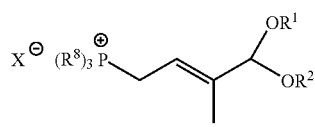
(Va)

in which $R^1$ and $R^2$ have the meaning indicated in claim 1, and $R^8$ is aryl and $X^-$ is an anion equivalent of an inorganic or organic acid, is employed in step b).

6. A process as claimed in claim 1, in which a sodium aluminum hydride compound is used as reducing agent in step c).

7. A process as claimed in claim 1, in which the compound of the formula VII is oxidized with oxygen in the presence of an N-oxyl radical and of a copper(I) compound in step d).

8. A compound of the formula

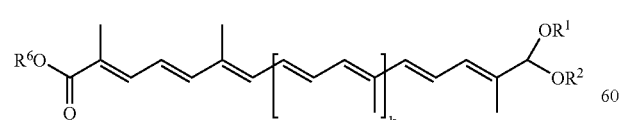

in which $R^1$ and $R^2$ are, independently of one another, $C_1$–$C_8$-alkyl or, together with the oxygen atoms to which they are bonded, and with the carbon atom located between them, are

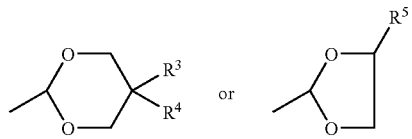

in which $R^3$, $R^4$ and $R^5$ are, independently of one another, hydrogen or $C_1$–$C_4$-alkyl,
$R^6$ is $C_1$–$C_8$-alkyl, and
k is 0 or 1,
when k is O, $R^1$ and $R^2$ together do not form the 5-membered hetero ring.

9. A compound of the formula

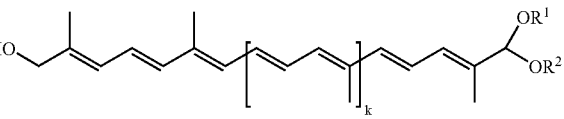

in which $R^1$ and $R^2$ are, independently of one another, $C_1$–$C_8$-alkyl or, together with the oxygen atoms to which they are bonded, and with the carbon atom located between them, are

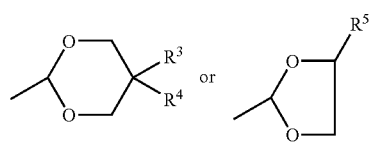

in which $R^3$, $R^4$ and $R^5$ are, independently of one another, hydrogen or $C_1$–$C_4$-alkyl, and
k is 0 or 1.

10. A compound of the formula

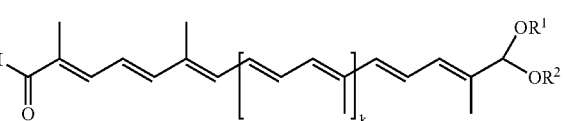

in which $R^1$ and $R^2$ are, independently of one another, $C_1$–$C_8$-alkyl or, together with the oxygen atoms to which they are bonded, and with the carbon atom located between them, are

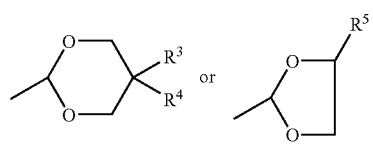

in which $R^3$, $R^4$ and $R^5$ are, independently of one another, hydrogen or $C_1$–$C_4$-alkyl, and
k is 0 or 1,
where $R^3$ and $R^4$ are not both methyl.

* * * * *